United States Patent
Gisiger et al.

(10) Patent No.: US 7,474,908 B2
(45) Date of Patent: Jan. 6, 2009

(54) METHOD FOR MEASURING THE TRANSCUTANEOUS $CO_2$ PARTIAL PRESSURE ON AN EAR LOBE

(75) Inventors: Pierre-Alain Gisiger, Laufen (CH); Dominik Liechty, Reinach (CH); Patrick Eberhard, Bottmingen (CH); Sohei Kagawa, Tokyo (JP)

(73) Assignee: Radiometer Basel AG, Basel (CH)

( * ) Notice: Subject to any disclaimer, the term of this patent is extended or adjusted under 35 U.S.C. 154(b) by 35 days.

(21) Appl. No.: 11/596,873

(22) PCT Filed: May 12, 2005

(86) PCT No.: PCT/CH2005/000265

§ 371 (c)(1), (2), (4) Date: Nov. 17, 2006

(87) PCT Pub. No.: WO2005/110221

PCT Pub. Date: Nov. 24, 2005

(65) Prior Publication Data

US 2008/0064942 A1 Mar. 13, 2008

(30) Foreign Application Priority Data

May 18, 2004 (CH) .................................. 867/04

(51) Int. Cl.
*A61B 5/05* (2006.01)

(52) U.S. Cl. ..................................... 600/354; 700/300

(58) Field of Classification Search .................. 700/300; 600/326, 323, 353–354, 358–359
See application file for complete search history.

(56) References Cited

U.S. PATENT DOCUMENTS

| | | | | |
|---|---|---|---|---|
| 4,333,473 A | * | 6/1982 | Eberhard et al. | 600/359 |
| 4,539,994 A | | 9/1985 | Baumbach et al. | 128/635 |
| 4,586,149 A | * | 4/1986 | Stillman et al. | 700/300 |
| 4,789,453 A | * | 12/1988 | Eberhard et al. | 204/403.13 |
| 4,805,122 A | | 2/1989 | McDavid et al. | 364/557 |
| 6,654,622 B1 | | 11/2003 | Eberhard et al. | 600/326 |

OTHER PUBLICATIONS

Lang, J.G. (1988) Apnea testing guided by continuous transcutaneous monitoring of partial pressure of carbon dioxide, Crit. Care Med. 26(5):868-872.

* cited by examiner

*Primary Examiner*—Charles A Marmor, II
*Assistant Examiner*—Anita Saidi
(74) *Attorney, Agent, or Firm*—Morgan, Lewis & Bockius LLP

(57) ABSTRACT

In a process for measuring partial transcutaneous $CO_2$ pressure on an earlobe by means of a sensor having a measuring device for measuring the partial transcutaneous $CO_2$ pressure and a heating system for heating a sensor contact surface for contact with the earlobe, the sensor contact surface is heated. During a first phase, the sensor contact surface is kept at an elevated temperature of at least 41.5° C. in order to prevent the measured value of partial transcutaneous $CO_2$ pressure from exceeding, due to the measurement process itself, the partial transcutaneous $CO_2$ pressure achieved after stabilization. The temperature of the sensor contact surface is then reduced to between 37° C. and 41° C. This facilitates considerably faster evaluation of the measured values.

13 Claims, 2 Drawing Sheets

Figures 4, 6:
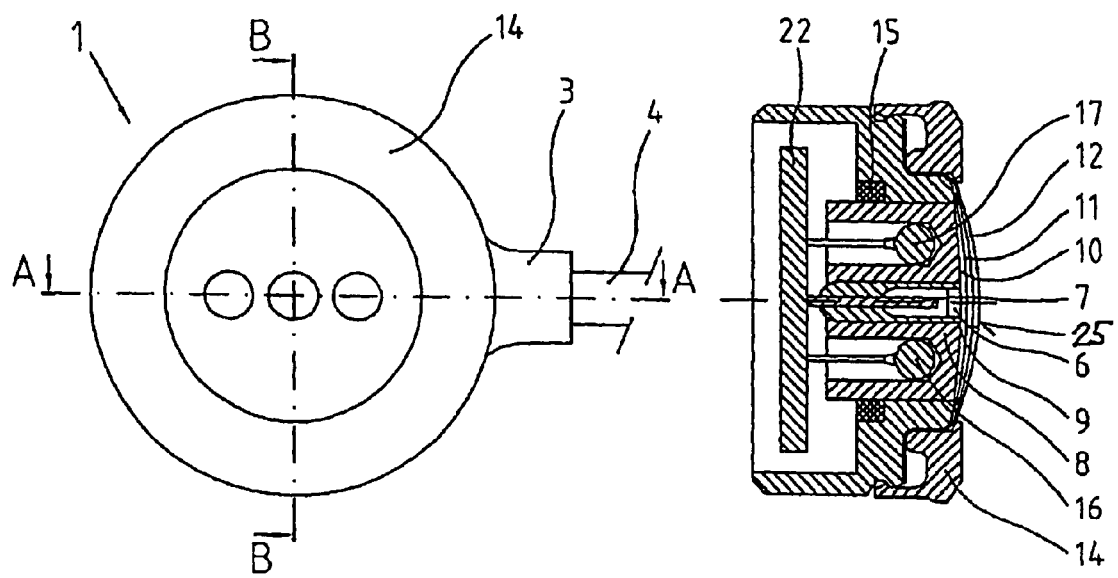

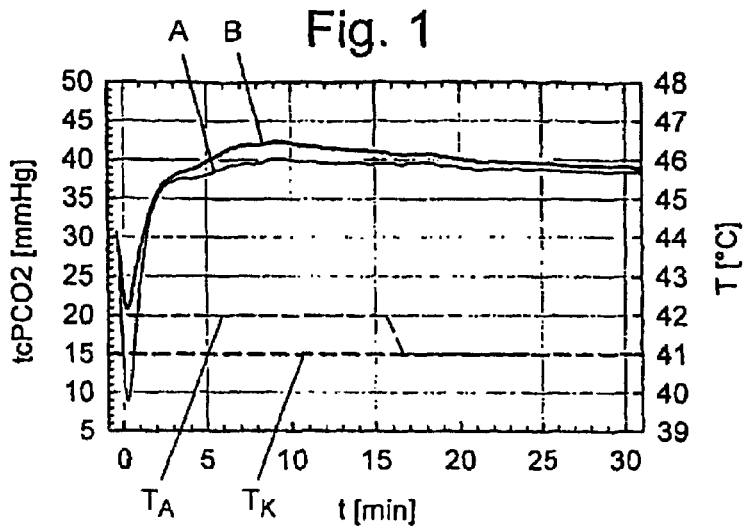
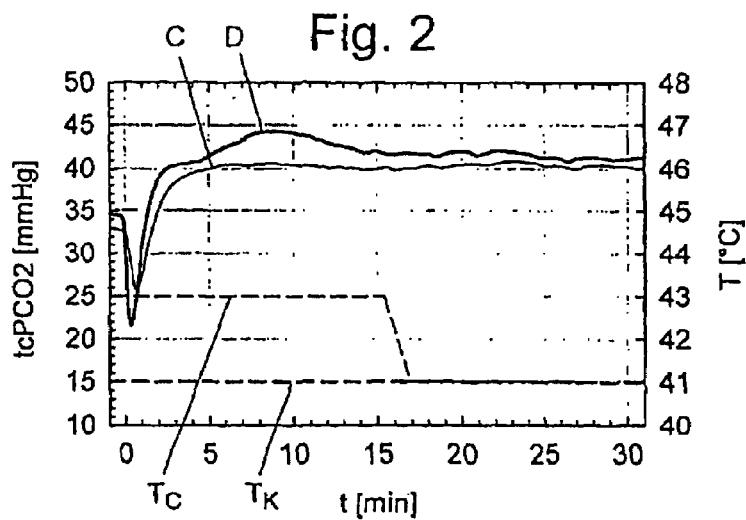
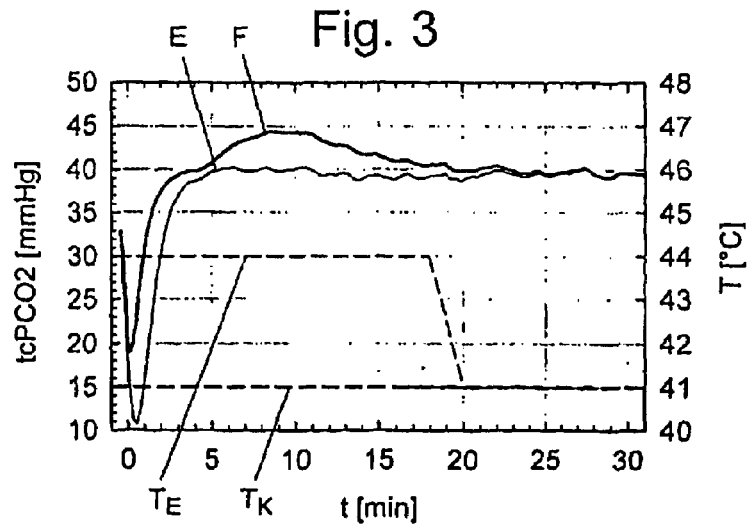

ured on blood samples taken show that approximately 20
METHOD FOR MEASURING THE TRANSCUTANEOUS $CO_2$ PARTIAL PRESSURE ON AN EAR LOBE The present application is a U.S. National Phase Application of International Application No. PCT/CH2005/000265 (filed May 12, 2005) which claims the benefit of Swiss Patent Application No. 867/04 (filed May 18, 2004), both of which are hereby incorporated by reference in their entirety.

The present invention refers to a method for measuring the transcutaneous partial pressure of carbon dioxide on an ear lobe, as defined in the preamble of the independent patent claim 1 and to a sensor for implementing this method, as defined in the preamble of the independent patent claim 8.

In order to be able to evaluate the respiratory functions of a patient it is often necessary to know the arterial partial pressure of $CO_2$ ($paCO_2$). There are various methods available today for measurement of the $paCO_2$ value, one of which includes measurement of the transcutaneous $CO_2$ partial pressure ($tcpCO_2$). This indirect method makes use of the fact that $CO_2$ diffuses easily through body tissues and skin. The gas is measured with a sensor applied to the surface of the skin, which is equipped with a heating element for heating the area of skin on which the sensor rests. If the sensor contact surface is heated to a temperature of about 40° C. to 44° C., then a local dilation and arterialization of the capillary bed is produced at the measurement site. Under these conditions, the transcutaneous $CO_2$ partial pressure measured there shows a high correlation with the arterial value. This makes it possible, with certain restrictions, to determine the $paCO_2$ value with sufficient accuracy for most applications.

Determining of the $paCO_2$ value by measurement of the transcutaneous $CO_2$ partial pressure offers several advantages: the measurement is non-invasive, continuous and may also be used with patients who are not intubated.

A method and a sensor for measurement of the transcutaneous $CO_2$ partial pressure on an earlobe as an advantageous measurement site are described in U.S. Pat. No. 6,654,622. In this, the sensor is attached on the earlobe using a clip or an adhesive strip. This requires no particular effort, and the measurement site is at a physiologically central place and is easily accessible and well visible, for example, for an anesthesiologist during surgery. Furthermore, hindrance of the operating surgeon or problems with respect to sterility requirements is extremely rare.

However, during measurements of the transcutaneous $CO_2$ partial on earlobes of patients with the sensors described in U.S. Pat. No. 6,654,622, unexpectedly high measurement values were recorded during the first 20 minutes with the sensor contact area at a temperature of approx. 41° C. The relevant measurement plots show an initial overshooting of the measurement values which begins about 5 minutes after application of the sensor and starts to decrease after about another 5 minutes until it is finally no longer observed approximately 20 minutes after the measurement is started. Direct comparative measurements of the arterial $CO_2$ partial pressure on blood samples taken show that approximately 20 minutes after the start of measurement the expected measurement values of the transcutaneous $CO_2$ partial pressure are achieved.

This overshooting of the transcutaneous $CO_2$ partial pressure in approximately the first 20 minutes after measurements are started means that the measurement values during this time cannot simply be used for the determination of the arterial $CO_2$ partial pressure. The arterial $CO_2$ partial pressure can therefore be determined using this known method for measuring the transcutaneous $CO_2$ partial pressure only after a relatively long start-up phase.

Therefore, the objective of the present invention is to provide a method for measuring the transcutaneous $CO_2$ partial pressure on an ear lobe in which the transcutaneous $CO_2$ partial pressure values measured are already usable for reliable determination of the arterial $CO_2$ partial pressure after a comparatively short start-up phase. Furthermore, a sensor should be provided with which such a method can be implemented.

This objective is accomplished by the inventive method and inventive sensor as defined in the independent patent claims 1 and 9. Patent claim 8 refers to an inventive method for preventing an overshoot of the transcutaneous $CO_2$ partial pressure in the skin of an earlobe over the $CO_2$ partial pressure achieved after stabilization during the arterialization of the skin. Preferred embodiments are provided in the dependent patent claims.

The invention can be characterized as follows: in a method for measuring the transcutaneous $CO_2$ partial pressure on an ear lobe the measurement takes place by means of a sensor, which has a measuring device for measurement of the transcutaneous $CO_2$ partial pressure and a heating element for heating a sensor contact surface intended for application on the earlobe. With this method the sensor contact surface is heated. The sensor contact surface is maintained at an elevated temperature of at least 41.5° C. during an initial phase to prevent a measurement-related overshoot of the measured value of the transcutaneous $CO_2$ partial pressure over the transcutaneous $CO_2$ partial pressure achieved after stabilization. Afterward, the temperature of the sensor contact surface is reduced to between 37° C. and 41° C.

Because the sensor contact surface is maintained at an elevated temperature of at least 41.5° C. during an initial phase, overshooting of the measurement value of the transcutaneous $CO_2$ partial pressure over the transcutaneous $CO_2$ partial pressure achieved after stabilization can be prevented. In this way, useful measurements are much faster achieved. The subsequent lowering of the temperature of the sensor contact surface to between 37° C. and 41° C. ensures that the patient suffers no burns at the measurement site.

It is assumed that the initial overshoot of the measurement value for the transcutaneous $CO_2$ partial pressure during measurements with a sensor contact surface temperature between about 37° C. and 41° C. is because the skin touching the sensor contact surface is in fact warmed quickly, which increases the local metabolism and thus leads to an increased release of $CO_2$, but that the cutaneous vasodilatation occurs later. This means that the metabolically produced $CO_2$ is only removed by the blood vessels later and the transcutaneous $CO_2$ partial pressure is initially in excess. Furthermore, the overshoot of the transcutaneous $CO_2$ partial pressure measurement could also be brought about or intensified by $CO_2$ stored in the skin.

After the preheating it is advantageous that the elevated temperature be reduced by at least 1° C., preferably by at least 2° C. This enables the selection of a sufficiently high increased temperature for the first phase without causing skin burns in the second phase after the temperature is decreased.

Preferably the elevated temperature is in the range of 41.5° C. to 44° C. This is sufficient to prevent an initial overshoot of the measurement value of the transcutaneous $CO_2$ partial pressure without the risk of skin burns during the relatively short initial phase.

It is advantageous that the initial phase with the elevated temperature, during which the sensor contact surface is applied on the earlobe, lasts between 5 and 60 minutes. Five minutes of increased temperature are sufficient in most cases to prevent an overshoot in the measurement of the transcutaneous $CO_2$ partial pressure. If 60 minutes of increased temperature are not exceeded, skin burns are practically excluded.

Preferably the first phase with the elevated temperature lasts between 6 and 30 minutes. In this way an overshoot of the transcutaneous $CO_2$ partial pressure measurement is effectively prevented. More than 30 minutes of elevated temperature offer no advantage in this regard. An optimal duration of the initial phase is considered to be between 6 and 15 minutes. An unnecessarily long initial phase has no advantage.

In a preferred embodiment the initial phase lasts between 6 and 30 minutes, and the elevated temperature is at least 42° C. In this way an overshoot of the transcutaneous $CO_2$ partial pressure is effectively prevented, and the elevated temperature is not maintained too long.

It is advantageous that the elevated temperature be approximately 44° C. and the first phase preferably last between 6 and 20 minutes. These conditions ensure that the measurement value of the transcutaneous $CO_2$ partial pressure will not overshoot in any case.

It is advantageous that the reduction of the temperature of the sensor contact surface take place at a rate of less than or equal to 1° C. per 10 seconds, preferably less than or equal to 1° C./min. If the temperature is lowered too quickly, a small peak may occur in the measurement curve. This means that measurements of the transcutaneous $CO_2$ partial pressure are influenced by the temperature reduction in such a way that their use for determining the arterial $CO_2$ partial pressure leads to imprecise results.

A further aspect of the invention consists of a method for prevention an increase of the transcutaneous $CO_2$ partial pressure in the skin of an earlobe over the $CO_2$ partial pressure achieved after stabilization during the arterialization of the skin during measurement of the transcutaneous $CO_2$ partial pressure. With this method the skin at a measurement site for the transcutaneous $CO_2$ partial pressure is maintained at an elevated temperature of at least 41.5° C. during an initial phase, and afterward the temperature of the skin is reduced to between 37° C. and 41° C.

As mentioned already above, during measurement of the transcutaneous $CO_2$ partial pressure on an earlobe, in which the sensor contact surface is heated to a temperature of between about 37° C. and 41° C., the skin touching the sensor contact surface warms more rapidly than cutaneous vasodilatation, i.e. arterialization of the skin, occurs. This means that the metabolically produced $CO_2$ is only removed by the blood vessels later and the transcutaneous $CO_2$ partial pressure is initially in excess. Furthermore, $CO_2$ is also stored in the skin; this increases the transcutaneous $CO_2$ partial pressure at first. The inventive solution counteracts this by maintaining the skin at a measurement site for the transcutaneous $CO_2$ partial pressure at an elevated temperature of at least 41.5° C., and afterward the skin temperature is reduced to between 37° C. and 41° C.

A sensor according to the invention has a measuring device for measurement of the transcutaneous $CO_2$ partial pressure and a heating element for heating of a sensor contact surface intended for application on an earlobe. Furthermore, it has a heater control with a timer, which reduces the heater power of the heating element after a predefined time so that the temperature of the sensor contact surface is reduced. The inventive method may be implemented with such a sensor, bringing the advantages cited.

It is advantageous that the predefined time after which the heater control reduces the heater power of the heating element be adjustable. This makes it possible to adjust the duration of the initial phase of elevated temperature, for example, as appropriate for the patient or patient group with which the sensor is applied. Thus, for example, it is conceivable that the initial phase for newborn infants be chosen to be shorter than for adults.

The measurement of the transcutaneous $CO_2$ partial pressure itself is based in general on an electrochemical principle. It is usually done potentiometrically by measuring the pH value of a thin layer of electrolyte solution, which is contacted with the skin via a hydrophobic membrane that is highly permeable to gas. A change of the transcutaneous $CO_2$ partial pressure on the skin surface causes a pH change of the electrolyte solution, which is proportional to the logarithm of the $tcpCO_2$ change. The pH value is determined, for example, by measuring the potential between a miniature pH glass electrode and a silver/silver chloride reference electrode. However, the present invention is not limited to this measurement procedure, but may rather be applied to any other methods for measuring the transcutaneous $CO_2$ partial pressure.

Figures 5, 7:
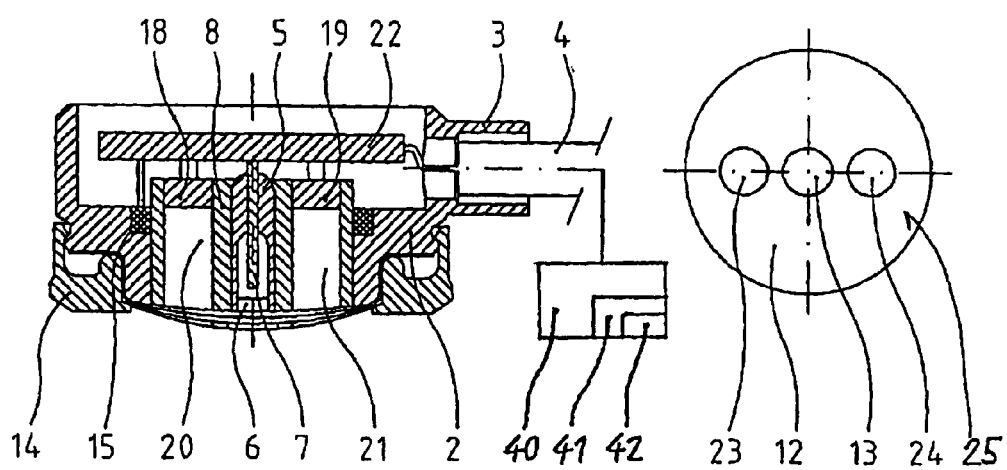

The inventive method and inventive sensor are described below with reference to the drawings included, based on embodiments. These show in FIG. 1—a chart with measurement curves for measurements of the transcutaneous $CO_2$ partial pressure on two earlobes of a test subject using sensors with sensor contact areas for which on one earlobe the sensor contact surface of the sensor is maintained at an elevated temperature of 42° C. during an initial phase;

FIG. 2—a chart with further measurement curves for measurements of the transcutaneous $CO_2$ partial pressure on two earlobes of the same test subject in which on one earlobe the sensor contact surface of the sensor is maintained at an elevated temperature of 43° C. during an initial phase;

FIG. 3—a chart with further measurement curves for measurements of the transcutaneous $CO_2$ partial pressure on two earlobes of the same test subject in which on one earlobe the sensor contact surface of the sensor is maintained at an elevated temperature of 44° C. during an initial phase;

FIG. 4—a schematic top view of an inventive sensor for the measurement of the transcutaneous $CO_2$ partial pressure and a pulse oximetric measurement of arterial oxygen saturation;

FIG. 5—a section view of the sensor cut along line A-A in FIG. 4;

FIG. 6—a section view of the sensor cut along line B-B in FIG. 4 and

FIG. 7—a top view of the sensor contact surface intended to be placed on an earlobe.

In the FIGS. 1-3, the X-axis of the charts represents the time in minutes, the left Y-axis is the partial pressure in mm Hg, and the temperature in degrees centigrade is specified on the right Y-axis.

On an earlobe of a test subject, the transcutaneous $CO_2$ partial pressure was measured in each case with a sensor in which the contact surface of the sensor was maintained at a constant temperature of 41° C. This constant temperature is represented in each case as a dashed horizontal straight line $T_K$. The corresponding measurements of the transcutaneous $CO_2$ partial pressure resulted in the measurement curve B in FIG. 1, the measurement curve D in FIG. 2 and the measurement curve F in FIG. 3. With all three of these measurement curves B, D and F it can be seen that the measurement values at first fall sharply from approximately 28-35 mm Hg to about 18-23 mm Hg, and after that rise to a peak of about 42-45 mm Hg, before they slowly drop to an approximately stable value of between 38 and 42 mm Hg.

The initial sharp decrease of the measurement values displayed results from removing the sensor from a calibration chamber and placing it on the earlobe. This means that the measurements for the first 3 to 5 minutes are not due to physiological conditions and therefore cannot be used for determining the arterial $CO_2$ partial pressure.

After that, overshooting occurs for the measurement values of the transcutaneous $CO_2$ partial pressure over the approximately stable value finally achieved; as explained above, this may be ascribed to the fact that the skin of the earlobe in contact with the sensor contact surface does in fact warm quickly, leading to an increase in the local metabolism and thus an increased release of $CO_2$, but cutaneous vasodilatation occurs later. This means that the metabolically produced $CO_2$ in the skin is only removed by the blood vessels later and the transcutaneous $CO_2$ partial pressure is initially in excess. Furthermore, the overshoot of the transcutaneous $CO_2$ partial pressure measurement could also be brought about or intensified by $CO_2$ stored in the skin.

In order to prevent this overshooting, in accordance with the invention the sensor contact surface of the sensor on the other earlobe of the test subject was maintained at an elevated temperature of 42° C., 43° C. and 44° C. respectively during an initial phase, and the temperature of the sensor contact surface was reduced to 41° C. only after this initial phase was over. For the measurement displayed in FIG. 1, the first phase lasted approximately 16 minutes and the temperature of the sensor contact surface (dashed temperature curve, $T_A$) was 42° C. during this time. Afterward, the temperature of the sensor contact surface was reduced by 1° C. within a minute. For the measurement displayed in FIG. 2, the first phase lasted approximately 15.5 minutes and the temperature of the sensor contact surface (dashed temperature curve, $T_C$) was 43° C. during this period. Afterward, the temperature of the sensor contact surface was reduced by 2° C. within one and a half minutes. For the measurement displayed in FIG. 3, the first phase lasted approximately 18 minutes and the temperature of the sensor contact surface (dashed temperature curve, $T_E$) was 44° C. during this period. Afterward, the temperature of the sensor contact surface was reduced by 3° C. within two minutes.

The measurement values of the transcutaneous $CO_2$ partial pressure associated with the temperature curves $T_A$, $T_C$ and $T_E$ resulted in the measurement curve A in FIG. 1, the measurement curve C in FIG. 2 and the measurement curve E in FIG. 3. For all three of these measurement curves A, C and E it can be seen that the measurements first drop sharply from 30-35 mm Hg to about 8-28 mm Hg, and thereafter rise rapidly to an approximately stable value between about 38 and 42 mm Hg. An overshoot of the measurements of the transcutaneous $CO_2$ partial pressure above the final approximately stable value reached is not to be seen. This means that the measurements are already usable after a relatively short warm-up phase of approximately 5 minutes.

FIGS. 4-7 show an embodiment of an inventive sensor for measurement of the transcutaneous $CO_2$ partial pressure, which may simultaneously perform a pulse oximetric measurement of arterial oxygen saturation. FIG. 4 shows a top view of a sensor 1, in which the cut surfaces of the cross section views for FIGS. 5 (A-A) and 6 (B-B) are drawn. The sensor head consists of a round housing 2 made of plastic with a neck-shaped extension 3, through which the connecting wires 4 are led out in FIG. 5 to a schematically represented measurement device 40. The components required for the measuring functions and the various electronic components described below are contained in the housing.

A glass pH electrode 5 is found in the centerline of the sensor. It consists of a cylindrical glass shaft onto the front side of which a pH-sensitive glass layer 6 has been fused. In the interior of the glass cylinder there is an internal reference electrode with a platinum lead-in wire 7 fused in the glass. The pH electrode 5 is embedded in a silver block 8 whose surface is covered with a chloride layer 9. The surface of the silver block thus forms an Ag/AgCl electrode, which serves as a reference electrode for the pH measurement. An electrolyte solution the pH value of which is measured is located in a porous, hydrophilic spacer 10, which is covered with a gas-permeable, hydrophobic membrane 11 (such as Teflon). To protect the membrane from mechanical damage it is covered with a metal faceplate 12. This faceplate has an opening 13 in the middle (over the pH-sensitive glass layer 6), through which the $CO_2$ gas to be measured can diffuse in the electrolyte solution in the area of the pH-sensitive glass layer. The spacer 10, the membrane 11 and the metal faceplate 12 are fastened to the sensor casing 2 by means of a tension ring 14. The silver block 8 also functions as a heater. It is wrapped like a spool with a heating wire 15, by means of which it is heated to a temperature between 37° C. and 45° C., which is required for the transcutaneous measurement. As can be seen in FIG. 6, there are two thermistors 16 and 17 embedded in two bore holes within the silver block 8. These thermistors 16, 17 serve to regulate and control the selected sensor temperature. The temperature of the sensor contact surface, which is usually lower, may be calculated from the temperature measured by the thermistors 16, 17. The temperature gradient to be used in the calculation may be determined beforehand by measuring the temperature at the sensor contact surface, in which case the temperature measurement follows the international standard IEC 60601-2-23, Clause 42. 3.104.

The optical components required for the pulse oximetric measurement can be seen in the cross section of FIG. 5. These are two LEDs 18 mounted directly adjacent to one another on a ceramic substrate, and a photodiode 19. The light from and to these components is channeled by two cylindrical light channels 20 and 21, which consist of two holes in the silver block filled with translucent material.

All electrical connections from and to the various components are run in an electronic unit 22, in which part of the signal processing is already performed. The connecting wires 4 to the measurement device 40 originate from this electronic unit and, as described, pass through the sensor neck 3 to the outside. The measurement device 40 has a heating control unit 41 with a timer 42, which in accordance with the invention may reduce the heater power of the heater constituted by the silver block 8 and the heating wire 15 after an adjustable, pre-determined time period.

Eventually, FIG. 7 shows a top view of the metal faceplate 12, which forms the actual contact surface 25 of the sensor. As already mentioned, a perforation 13 is located in the center of the faceplate, through which the carbon dioxide gas can reach the electrolyte at the pH electrode. The two perforations 23 and 24 arranged on the periphery permit the outgoing light from the LED and scattered light from the tissue to pass through.

Further embodiments of the inventive method and sensors described above can be implemented. It is explicitly noted here that the sensor, of course, need not have components for performing a pulse oximetric measurement of the arterial oxygen saturation. Furthermore, the entire electronics for measurement may also be situated in the sensor head itself.

The invention claimed is:

1. A method for measurement of the transcutaneous $CO_2$ partial pressure on an ear lobe by means of a sensor which has a measuring device for measurement of the transcutaneous $CO_2$ partial pressure and a heating element for warming a sensor contact surface intended for contact with the ear lobe, said method comprising:
   maintaining the sensor contact surface at an elevated temperature of at least 41.5° C. during an initial phase; and
   subsequently reducing the temperature of the sensor contact surface by a temperature reduction rate to between 37° C. and 41° C.,
wherein the temperature reduction rate is less than or equal to 6° C. per minute.

2. The method according to claim 1, wherein the temperature reduction rate is less than or equal to 3° C. per minute.

3. The method according to claim 1, wherein the temperature reduction rate is less than or equal to 1° C. per minute.

4. A method according to claim 1, wherein the temperature is reduced by at least 1° C.

5. The method according to claim 1, wherein the elevated temperature is in the range of 41.5° C. to 44° C.

6. The method according to claim 1, wherein the initial phase lasts between 6 and 30 minutes.

7. The method according to claim 6, wherein the elevated temperature is at least 42° C.

8. The method according to claim 7, wherein the initial phase lasts between 6 and 20 minutes and wherein the elevated temperature is approximately 44° C.

9. A sensor for implementation of the method according to claim 1, comprising:
   a measuring device for measuring the transcutaneous $CO_2$ partial pressure and a heating element for heating of a sensor contact surface intended for contact with an earlobe,
wherein the sensor comprises a heater control with a timer which reduces the heating power of the heating element after a predefined period, so that the temperature of the sensor contact surface is reduced.

10. The sensor according to claim 9, wherein the predefined period is adjustable.

11. A method for prevention an increase of the transcutaneous $CO_2$ partial pressure in the skin of an earlobe over the $CO_2$ partial pressure achieved after stabilization during the arterialization of the skin with the measurement of the transcutaneous $CO_2$ partial pressure, said method comprising:
   maintaining the skin at a measurement site for the transcutaneous $CO_2$ partial pressure at an elevated temperature of at least 41.5° C. during an initial phase and
   subsequently reducing the temperature of the skin by a temperature reduction rate to between 37° C. and 41° C.
wherein the temperature reduction rate is less than or equal to 6° C. per minute.

12. The method according to claim 11, wherein the temperature reduction rate is less than or equal to 3° C. per minute.

13. The method according to claim 11, wherein the temperature reduction rate is less than or equal to 1° C. per minute.

* * * * *